United States Patent [19]

Nagel

[11] 4,211,237
[45] Jul. 8, 1980

[54] METHOD AND APPARATUS FOR IDENTIFYING RECURRING SIGNAL PATTERNS

[75] Inventor: Joachim Nagel, Beckingen, Fed. Rep. of Germany

[73] Assignee: Biotronik Mess- und Therapiegeräte GmbH & Co., Berlin, Fed. Rep. of Germany

[21] Appl. No.: 896,771

[22] Filed: Apr. 14, 1978

[30] Foreign Application Priority Data

Apr. 14, 1977 [DE] Fed. Rep. of Germany ....... 2716739

[51] Int. Cl.² ............................................. A61B 5/04
[52] U.S. Cl. .................................... 128/698; 364/417
[58] Field of Search ...................... 128/2.06 B, 2.06 A, 128/2.06 R, 2.06 F, 696, 698, 702, 703, 704, 706, 708, 901, 902; 364/415, 417, 728, 819

[56] References Cited

U.S. PATENT DOCUMENTS

| | | | |
|---|---|---|---|
| 3,755,783 | 8/1973 | Astarjian et al. ................ | 128/2.06 A |
| 3,811,428 | 5/1974 | Van Horn et al. ................ | 128/2.06 B |
| 3,861,387 | 1/1975 | Lawhorn et al. ................ | 128/2.06 A |
| 3,878,833 | 4/1975 | Arneson et al. ................ | 128/2.06 A |
| 3,940,692 | 2/1976 | Neilson ............................ | 128/2.06 A |
| 4,023,564 | 5/1977 | Valiquett et al. ................ | 128/2.06 A |
| 4,086,652 | 4/1978 | Mantz .................................. | 364/819 |

Primary Examiner—William E. Kamm
Attorney, Agent, or Firm—Spencer & Kaye

[57] ABSTRACT

A periodically occurring signal pattern that is part of a signal mixture including interference components, in particular QRS complexes of fetal heart signals in an abdominally derived fetomaternal electrocardiogram, is detected by storing the amplitude-time waveform pattern of a signal that has initially been recognized according to a first criterion, preferably an amplitude criterion, in a memory and then using this pattern for identifying subsequent signals according to a second criterion which is the degree of coincidence of the signal in question with the amplitude shape of the stored pattern.

43 Claims, 12 Drawing Figures

$$R_{SM}(0)\big|_{t=t_1} = \frac{1}{T}\int_0^T S(t+t_1-T)\cdot M(t)\,dt$$

METHOD AND APPARATUS FOR IDENTIFYING RECURRING SIGNAL PATTERNS

BACKGROUND OF THE INVENTION

The present invention relates to a method for identifying periodically occurring like signals that are part of a signal mixture including interference components, particularly for detecting QRS complexes of fetal heart signals in an abdominally derived fetomaternal electrocardiogram, as well as to an apparatus for practicing the method.

The detection and identification of periodically occurring like signals in a signal mixture containing interference signals represents a goal which has not yet been satisfactorily reached in, for example, perinatalogy where it is desired to detect and process fetal electrocardiograms (EKGs). A fetal EKG cannot be derived directly from the fetus with the aid of scalp electrodes until immediately preceding birth, after the amnionic sac has broken. Since, therefore, this cannot be done during the entire period of pregnancy, methods of indirectly deriving the fetal EKG from the mother must be used if effective monitoring of the fetus is to be achieved. However, electrical signals derived from the mother's abdomen have a very unfavorable signal to noise ratio so that the discovery quota for the occurrence of fetal QRS complexes with the prior art filtering techniques is only about 50%. A fetal QRS complex is a characteristic component of the heart signal, specifically a signal occurrence containing P, Q and R peaks. Since this is sufficient, at most, to indicate the average fetal heart frequency, the physician has available to him neither sufficient data about microfluctuations, i.e., temporary fluctuations in the heart frequency, nor about the wave shape of the fetal EKG.

Interfering with the fetal EKG are the maternal EKG, the maternal electromyogram signals due to muscle movements and noise signals. Their amplitudes are much higher than that of the fetal electrocardiogram whose maximum amplitude when recorded by means of abdominal electrodes is 10 to 50 $\mu V$. The amplitude of the fetal EKG changes considerably, however, depending on the position of the fetus with respect to the electrodes.

A maternal abdominal signal has the following composition:

$$S(t) = D(t) \cdot [E_f(t) + E_m(t) + N(t)]$$

where
S(t) = abdominal signal
D(t) = multiplicative distortion
$E_f(t)$ = fetal EKG
$E_m(t)$ = maternal EKG
N(t) = noise and maternal electromyogram The interferences from $E_m(t)$ and N(t) are additively superposed on the fetal EKG. The additional multiplicative distortions originate mainly from movements which occur but their influence is so slight that a good approximation can be reached if they are ignored, in which case the result will be:

$$S(t) = E_f(t) + E_m(t) + N(t).$$

The wave shapes of the individual components are not known in advance and are often even subject to fluctuations within the time interval in which the signals are being processed so that evaluation is made substantially more difficult.

The maternal QRS complex has its greatest power density in the frequency range between 10 and 30 Hz. The maximum of the fetal QRS complex in the frequency spectrum is a bit higher, i.e., between 15 and 40 Hz.

The noise components contained in the abdominal signal extends over the entire frequency range. Very low frequency noise probably originates mainly from movement of the electrodes, while the higher frequency portion must be attributed to the electromyogram.

In practice, the following methods have been used to detect the fetal electrocardiogram in the abdominal signal:

Differential method

In addition to the abdominal EKG, a normal EKG is recorded from the mother. By subtracting the two EKG's it is attempted to eliminate the maternal EKG from the abdominal signal. This method is fraught with errors since it is practically impossible to bring the two maternal EKG's into coincidence with respect to amplitude and phase. Noise signals are not suppressed. This method is therefore unsuitable, particularly for routine examinations.

Blanking Method

The maternal EKG controls an electronic switch which blanks out the abdominal EKG as soon as a maternal QRS complex occurs. With this method it is impossible to detect fetal QRS complexes which wholly or partly coincide with the maternal complexes.

Amplitude Discrimination

The abdominal EKG controls two trigger circuits set to different threshold values. When the upper threshold value is exceeded, this indicates the occurrence of a maternal QRS complex, while the exceeding of the lower threshold indicates a fetal QRS complex. This method has the same drawbacks as the blanking method.

All three of the methods described above are very unreliable if interfering pulses are present.

A signal analysis proposed by Christiansen and Hoegl in an article entitled (in translation) "Development of a device for measuring the fetal electrocardiogram before and during birth," published in Biomedizinische Technik (Biomedical Art), volume 20, issue No. 5, 1975, proceeds according to basically the same method. However, instead of the signal amplitude proper, its first derivative is examined. This does not result in greater reliability of QRS complex recognition.

Selective Filters

The greatest accuracy in detecting interference with signals according to the prior art is offered by selective filters. The best solution for locating a signal of known waveform is the optimum search filter, or matched filter. The selective filters previously employed to effect a "beat-to-beat" recognition of the fetal QRS complex, however, do not have the structure of an optimally matched filter and therefore do not operate reliably. The output of the matched filter furnishes the autocorrelation function (ACF) of the useful signal. However, since the wave shape of the signal being searched for is not known, it is impossible to design a search filter specially adapted to this case.

All of the known methods have in common that error registrations result which have their origin in the unfavorable ratio of the interference components to the detected signals even after processing according to the respective methods. The theoretical quality factor of a matched filter cannot even be approximated by any of these methods.

German Offenlegungsschrift (Laid Open application) No. 1,807,147, discloses a wave shape detector which makes it possible to detect a known wave shape in a signal mixture by means of a correlation process. However, this detector is unable to detect a wave shape whose curve is not known beforehand.

SUMMARY OF THE INVENTION

It is therefore an object of the present invention to provide a method and an apparatus for practicing the method which permit reliable detection of periodically occurring like signals in a signal mixture containing interference components with special adaptation of the detecting process to the present state of the signal to be recorded, in which the exact shape of the signal to be detected need not be known beforehand.

It is a further object of the invention to improve the detection of a selected signal pattern by removing from the signal mixture characteristic interference components which are superimposed, in the mixture, on the selected signal pattern.

The method according to the invention can be practiced by an appropriate measuring device and requires a small number of calculating operations so that measurements can also be made quickly and reliably even by technically untrained personnel. After detecting the signal it is moreover possible to reproduce its wave shape.

These and other objects according to the invention are achieved by a method for detecting similar periodically recurring signal segments contained in a signal mixture which also contains interference signal components, particularly for detecting the QRS complexes of fetal heart signals contained in an abdominally derived fetomaternal electrocardiogram, which method includes detecting the amplitude-time pattern, or waveform, of a signal according to a first criterion, storing that signal as a sample in a memory, and then utilizing the stored sample to identify subsequently occurring signal segments according to a second criterion by determining the degree of coincidence of each such signal segment with the pattern of the stored sample.

A particular advantage of the process according to the invention is that it permits signal evaluation in real time so that the results are available immediately once a short starting phase has been completed. Each individual signal train or segment is recognized directly. The evaluation process automatically adapts itself to a change in the time of the input signals so that it is always possible to optimally detect the interfered with signals according to the circumstances at hand. The evaluation results correspond, in a good approximation, to those that can be realized with a matched filter.

A medical examination device operating accoridng to the method of the invention is particularly suited for routine examinations due to its simple operability as a result of the automatic evaluation process and reliable detection of the signals to be monitored. It is therefore suitable for a broad field of applications, for example, also for recording myosignals. With a few additional means it is possible to display the wave shape of the fetal electrocardiogram at any time.

One of the possible solutions according to the invention is based on a signal analysis by means of correlation. The calculation of the ACF of the signal is independent of the shape of the signal and can therefore also be effected if the signal to be expected is not known beforehand. There only exists the possibility of detecting the EKG on the basis of its periodicity which remains intact in the ACF. Since, however, the interval between two QRS complexes is not constant but subject to great fluctuations, and since the maternal EKG which is present as interference is also periodic, it is not possible to derive a reliable recognition of each individual heart beat therefrom. This drawback of correlation analysis could be overcome in that it was possible to determine the wave shape of the signal being monitored by a parallel process and to make an analysis with the aid of the cross correlation function (CCF) according to a matched filter method utilizing this pattern. This is done according to an advantageous embodiment of the present invention.

The present invention is based on the realization that in a process for detecting signals whose wave shape or pattern is unknown and which occur moreover at variable intervals, there must exist a way to adapt the process to the differing states of the signal. By determining the wave shape or pattern of the signal which has initially been detected with some certainty by one method and basing the later recovery, or detection of that signal or a like signal on this signal shape, the drawbacks of the known methods are avoided. Once the desired signal has been detected in a starting phase of the measurement, for example during a period of time when an interference signal that is repeated at intervals in time happens to be absent, the sensitivity of the process is increased in such a manner that useful signals on which interference signals are superposed are detected with regularity. This characteristic is of particular importance if it is required, as is the case for an electrocardiogram to precisely determine the repetition frequency of the signal and the fluctuations occurring therein.

Further advantageous embodiments of the method according to the invention will be described in detail below.

The evaluation of a fetomaternal EKG will be used as an example to explain how the desired signal is initially recognized by utilization of the autocorrelation function, while the later recovery of the signal is effected by forming the cross correlation function between the retained or stored signal pattern and the current signal shape.

The autocorrelation function of a signal is generally defined by $$R_{SS}(\tau) = \frac{1}{2T} \cdot \int_{-T}^{+T} S(t) \cdot S(t - \tau) dt$$

If the component $E_m(t)$ is substantially suppressed, in a manner to be described, below the remaining abdominal signal $S(t)$ can be split into the terms $E_f(t)$ and $N(t)$, so that $S(t) = E_f(t) + N(t)$, and the following applies for the autocorrelation function:

$$R_{SS}(\tau) = R_{EE}(\tau) + R_{NN}(\tau) + R_{EN}(\tau) + R_{NE}(\tau), \quad (1)$$

Where E is the fetal EKG, N is the superposition including the maternal electromyogram, noise components and remainders of the suppressed maternal EKG, $R_{EE}(\tau)$ is the autocorrelation function component for $E_f$, $R_{NN}(\tau)$ is the autocorrelation function component for N, and $R_{EN}(\tau)$ and $R_{NE}(\tau)$ are the cross correlation function components for $E_f(\tau)$ and $N(t-\tau)$, and $N(t)$ and $E_f(t-\tau)$, respectively.

The ACF of the interference coincidence $R_{NN}$ has a maxamin at $\tau=0$, which will no longer be reached at $\tau>0$. The ACF of the useful signal, $R_{EE}$, has a periodic maximum that lies at $\tau=k\cdot T_f (k=0, 1, 2, \ldots)$, where $T_f$ is the period between two successive fetal QRS complexes. If it is assumed that the cross correlation components, $R_{EN}$ and $R_{NE}$, and $R_{NN}$ are small for $\tau>0$ compared to the maxima of $R_{EE}$, and the spacing between two QRS complexes is constant, then it is possible in principle to detect the fetal EKG by determining the maxima at $\tau>0$.

Although these assumptions constitute only rough approximations of the actual conditions, it is possible in this way to realize a noticeable improvement in the reliability of the signal analysis compared to prior art methods. However, when there are distinct interference signals and when there are great demands for accuracy of the original determination, the resulting detection reliability is insufficient. Moreover, calculation of the ACF is too complicated for practical use since the integral must be calculated for at least the entire range from $\tau=0$ to $\tau=T_f$.

If it is assumed that the power of the signal to be detected in the signal mixture in question is greater than the power of the interference contained therein, the signal can be localized by a calculation of the ACF for $\tau=0$, i.e., by measuring the power. This results in a significant reduction of the calculating efforts required. If during the recording of a fetal electrocardiogram the signal power exceeds a previously set level, it is concluded that a QRS complex is present.

In accordance with a preferred embodiment of the invention the maximum of the ACF is determined for a given period of time. In a method for determining the signal level during detection of QRS complexes of fetal heart signals in the fetomaternal electrocardiogram, this advantageously extends over the duration of a plurality of maternal heart signal cycles.

The reliability of the signal detection is sufficient to use the rise in the level of the signal obtained by autocorrelation as the triggering pulse for initiating the recording process of the signal detected in the signal mixture as a sample for further signal detection. The accuracy of this sample is improved during the course of the process by average formation with later recorded signals and the sample is thus brought up to date.

The further signal detection is effected with the aid of this sample by cross correlation analysis. A CCF can be derived from the abdominal signal $S(t)$ and the sample EKG $M(t)$. $M(t)$ is the group average (average waveform) of the fetal EKG $E_f(t)$. This CCF has the following composition:

$$R_{SM}(\tau) = \frac{1}{2T} \cdot \int_{-T}^{+T} S(t) \cdot M(t-\tau) dt$$

where $$S(t) = E_f(t) + N(t)$$

consequently $$R_{SM}(\tau) = R_{EM}(\tau) + R_{NM}(\tau)$$

and due to $$M(t) \triangleq E(t)$$

$$R_{SM}(\tau) = R_{EE}(\tau) + R_{NE}(\tau) \qquad (2)$$

The difference between the previously described ACF and this CCF is:

$$R_{SS} - R_{SM} = R_{NN} + R_{EN}. \qquad (1)-(2)$$

Thus the CCF has a substantially better signal to noise ratio than the ACF. The results that can be realized in this way meet clinical requirements.

During signal analysis, the CCF for $\tau=0$ is calculated for every point in time $t_i$. A digital calculation is then made according to the formula $$R_{SM}(t) = \frac{1}{P} \cdot \sum_{k=0}^{P-1} S[k \cdot \Delta t + t - (P-1)\Delta t] M(k \cdot \Delta t)$$

where $\Delta t$ is the time interval between two successive scanning points. P is the number of supporting points used to calculate the CCF.

The accuracy of the analysis depends on the number of supporting points used to calculate the CCF.

As is the custom in the correlation art, the signal evaluation in the process according to the invention is effected, if a time sequence is of importance, by evaluation or storage, respectively, of amplitude values occurring at different points in time. In this case, a compromise must be made under consideration of the desired accuracy as well as the circuitry involved. In an advantageous embodiment of the present invention, a conclusion is made at a point in time $t_i$, at which the CCF which is normalized to 1 exceeds a given threshold value, that there exists a fetal QRS complex in the abdominal EKG. Once the CCF has reached its maximum the sample EKG and the fetal EKG contained in the abdominal signal are of identical phase. A trigger signal derived therefrom is able to control adaptation of the sample to the actual EKG by the above-mentioned average formation which can then likewise be made exponentially.

Since the amplitude of the fetal EKG is subject to time fluctuations, it is of advantage to provide for variation of the triggering threshold, the exceeding of which by the correlation function (CF) indicates the presence of a fetal QRS pulse and, on the other hand, initiates the recording of the heart signal as a sample or its processing in the form of an average formation, respectively, so that the signal detection process adapts itself to fluctuations in the level of the input signal.

Sometimes it happens that the interfered with signal mixture contains other signals which are similar to one another, like the useful signal, and which occur at intervals but which are unwanted since they interfere with the detection of the useful signals. In the analysis of fetal EKG's the maternal heart signal $E_m(t)$ constitutes such an interference. Because this signal is of a type very much like the fetal heart signal $E_f(t)$ to be detected and because the amplitude of $E_m(t)$ exceeds that of $E_f(t)$ by a multiple, the $E_M(t)$ signal constitutes a considerable impediment to the detection of the fetal heart signal, $E_f(t)$.

In an advantageous embodiment of the method according to the invention this difficulty is overcome in that like signal components such as the $E_m(t)$ segments, which recur at intervals and exceed a certain amplitude level are detected and eliminated from the signal mixture by subtraction. It is important that upon the occurrence of such an interference signal the actual signal form is not substracted since then a zero level would appear at the output. Instead a signal is subtracted which has been obtained by average formation of past detected signals, this being advisably again effected by exponential averaging.

Thus in the detection and monitoring of the fetal EKG, the maternal EKG is subtracted from the abdominal signal before the correlation analysis so that sufficient assurance is given that the fetal EKG can be detected even when analyzing electrocardiograms with heavy interference.

In order to be able to effect optimum signal detection, a preferred embodiment of the invention provides that the interfered signal is prefiltered before the detection process is employed to permit passage of only those frequency components which are contained in the signal to be found.

If it is desired at a later time to display the time sequence of the signal to be detected, the original signal pattern can be reconstructed by suitable inverse filtering.

An improvement in interference suppression can be realized if the amplitude of the stored sample is adapted, for subtraction, not to the amplitude of the signal mixture but to the amplitude of the interference signal which is contained in the mixture and is to be suppressed. This is of particular advantage if the amplitude of the useful signal is not much less than that of the interference signal. The fact that the interference signal and signal mixture maxima deviate considerably from one another would otherwise produce errors in the subtraction process. Since the amplitude of the interference signal contained in the signal mixture cannot be measured directly before its separation, such adaptation initially seems to be impossible. However, it has been found to be possible to solve this problem by utilizing signal statistics. A particularly advantageous method provides for the calculation of a scaling factor K for amplitude matching from the ratio of the cross correlation function between sample and signal of the ACF of the sample, or to the cross power between sample and signal and the power of the sample. This results in a scale which depends only on the interference signal itself and thus is theoretically free of errors. The cross power spectrum and the cross correlation function are Fourier transformed pairs such as the power spectrum and the autocorrelation function.

The advantage of the use of ACF and CCF in connection with the entire process is that components included in the circuit in any case (e.g. the correlator) can be used for this purpose as well.

As an explanation:

$$S(t) = E(t) + N(t)$$

where
$S(t)$ = the signal mixture to be processed;
$E(t)$ = the interference signal to be suppressed:
$N(t)$ = the useful signal (fetal EKG) and
$E(t) = k \cdot M(t)$ where
$M(t)$ = the sample of the interference signals.
The following is assumed to apply:

$$S(t) - k \cdot M(t) = N(t), \qquad (3)$$

k is to be found and N(t) is unknown.
Multiplying both sides of (3) by M(t):

$$S(t) \cdot M(t) - k \cdot M(t)^2 = N(t) \cdot M(t)$$

Integration then yields:

$$\int S(t) \cdot M(t) dt - k \int M(t)^2 dt = \int N(t) \cdot M(t) dt$$

or:

$$R_{SM}(0) - k \cdot R_{MM}(0) = R_{NM}(0)$$

If sample and useful signal are uncorrelated, their cross correlation function $R_{NM}(0) = (0)$ Consequently: $k = R_{SM}(0)/R_{MM}(0)$ and due to $R_{SM} = R_{EM} + R_{NM}$ with $R_{NM} = 0$ it follows that k is independent of N(t).

The scaling factor K is thus determined as the quotient of the CCF between signal and sample and the ACF of the sample. This corresponds to the quotient of the cross power between signal and sample and the power of the sample.

In the method according to the invention it is thus important to detect in an interfered with signal mixture a desired signal once or several times. If the amplitude criterion is employed for the signal detection the threshold value is advisably above the sensitivity threshold that will be realized later on in the process. These detected signals are used as "sample" for detecting signals that are hidden in the signal mixture and cannot be easily recognized. In order to realize further improvement in the sample signal, use can be made of either the original criterion or of a control signal which has been obtained from a comparison of the interfered with signal mixture with the sample signal with respect to similarities.

Either the averaged signal can then be evaluated as the desired signal found in the interfered with signal mixture, in which case the last detected signal is also included in the averaging, or the averaged signal can be used for the subtractive removal of the signal forming an interference from the signal mixture before a final evaluation is made.

In this case the last detected signal should not be included in the average formation before subtraction since, if it constitutes a time segment of the signal mixture, it also contains the desired signal in a superposed signal component which, in order to produce freedom from interference by subtraction, should not be included in the subtrahend.

Due to the fact that the process according to one invention permits the detection of, on the one hand, a desired signal and, on the other hand, an interference signal, both signal shapes being initially unknown and the desired signal being evaluated after the detected interference signal is removed, the invention opens the possibility of separating the desired signal from such an interference signal even in a signal mixture where both signals are relatively similar to one another. It is only necessary to provide for separate recognition of the two signals by way of a first criterion in the starting phase of the measurement and to store them, so as to be able to use them as a sample signal for later recognition of the signal or the interference, respectively. In this case the desired signal may, for example, have a substantially lower amplitude than the interference signal.

An apparatus for practicing the method according to the invention is realized with advantage by using one or a plurality of microprocessors.

Variations of two preferred embodiments of the invention are illustrated in the drawings.

BRIEF DESCRIPTION OF THE DRAWINGS

FIG. 7b is a circuit diagram of an analog version of the maximum detector of FIG. 7a.

DESCRIPTION OF THE PREFERRED EMBODIMENTS

Figure 1:
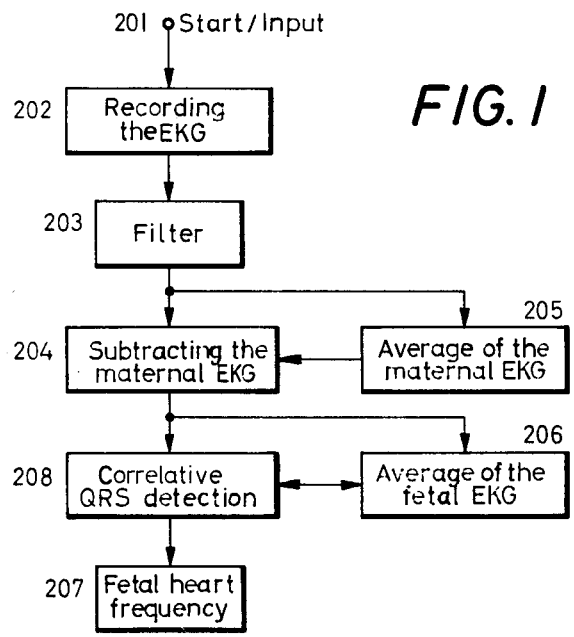
FIG. 1 is a basic block diagram illustrating the signal processing sequence of the present invention which is common to all embodiments.

FIG. 1 is a basic illustration of the operating sequence of the method according to the invention which sequence is performed in the embodiments described hereinbelow. The sequence is thus shown in general terms applicable to all embodiments and variations thereof described hereinafter. The individual illustrated stages may be either circuits that are constituted by electronic components or by routines of a computer program, which is effected in real time by a suitable computer. Point 201 represents either the input of the circuit or the starting point of the computer program. Stage 202 performs all operations connected with recording the EKG.

Figure 2:
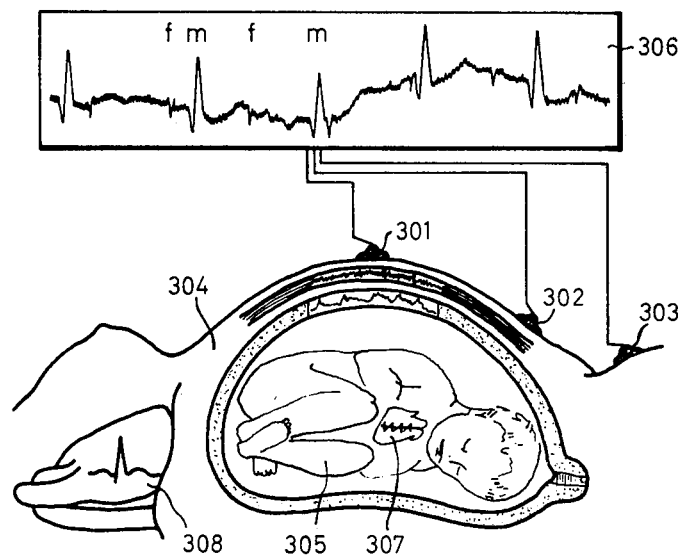
FIG. 2 is a simplified pictorial view illustrating the way in which signals are obtained.

FIG. 2 shows the recording of a fetomaternal EKG. Various electrodes, 301, 302 and 303 are fastened to the body of a female patient in order to receive signals to determine the electrocardiogram of a fetus 305. In the signal curve 306 recorded by means of pickups 301 to 303, the signal from the heart 307 of the fetus is superposed on the signal from the heart 308 of the mother together with various interference components. The fetal and the maternal heart signals are identified several times in the signal curve 306 as "f" and "m," respectively.

In a filter stage 203 the received fetomaternal heart signal is freed of interfering signal components and in the subsequent stage 204 the maternal heart signal is removed from the filtered input signal by subtraction. What is subtracted in stage 204 is a signal shape which corresponds to the average of the maternal EKG in that the maternal EKG is detected by a maximum value detector and in the course of formation of the average value, that value is continuously corrected or brought up to date. In the first two variations of the method, the maximum value criterion is retained over the total period or the maximum value criterion is used in a starting time period, for the autocorrelation function of the input signal, while at a later point in time, when the maternal electrocardiogram has been recognized with sufficient certainty, it is based on the detection of the maximum of the cross correlation function between the stored signal shape and the input signal so that only a signal similar to the stored signal shape is utilized for the average formation and thus for a correction of the signal shape. The average of the maternal EKG is retained, or stored, in stage 205.

During subtraction, the amplitude of the signal to be subtracted is matched with the amplitude of the input signal and the scaling factor K, which determines the amplitude of the signal to be subtracted, is formed from the ratio of the amplitude of the stored maternal EKG to the amplitude of the input signal, i.e. the maximum of the actual maternal QRS complex. Or, if according to another variation of the method, correlation functions are formed in this stage, the scaling factor K can be formed from the ratio of the cross correlation function between the stored sample EKG and the input signal to the autocorrelation function of the sample signal.

In the subsequent stage 208, the fetal EKG signal is actually determined and, according to the invention, the presence of a fetal heart signal is first detected by means of a maximum criterion while during the later course of the process the second criterion is used to determine the presence of a fetal heart signal from the degree of coincidence between the shape of the input signal and the shape of the stored average value, i.e. the sample signal. The average of the fetal EKG is stored in stage 206, while in stage 207 the fetal heart frequency is calculated from the time periods of the fetal heart signals and is stored there.

Figure 3A:
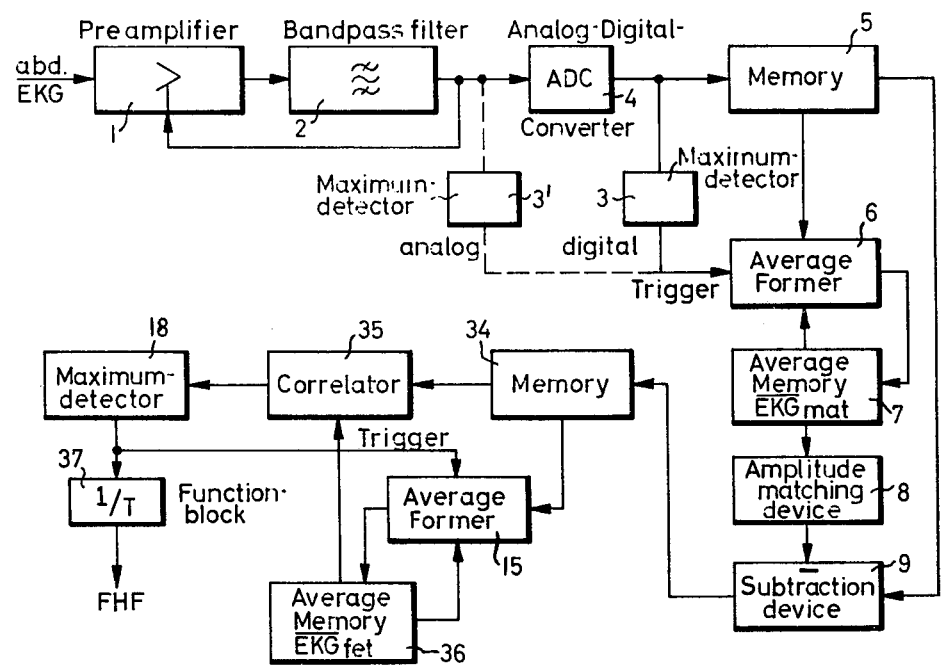
FIG. 3a is a block circuit diagram of a first advantageous embodiment of the apparatus according to the invention.
Figure 3B:
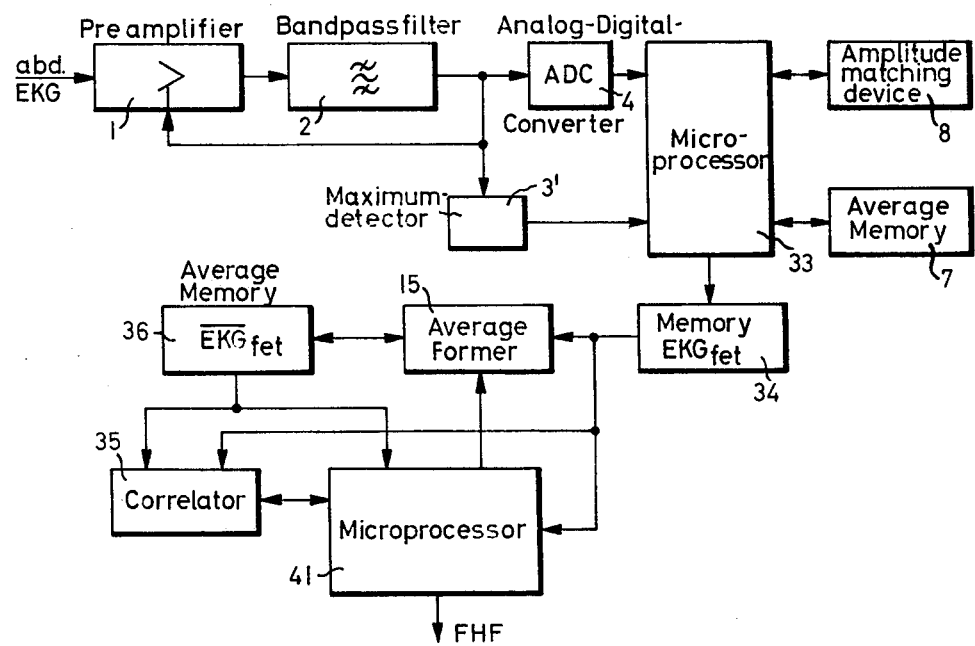
FIG. 3b is a block circuit diagram of a second embodiment of the invention utilizing a microprocessor.
Figure 3C:
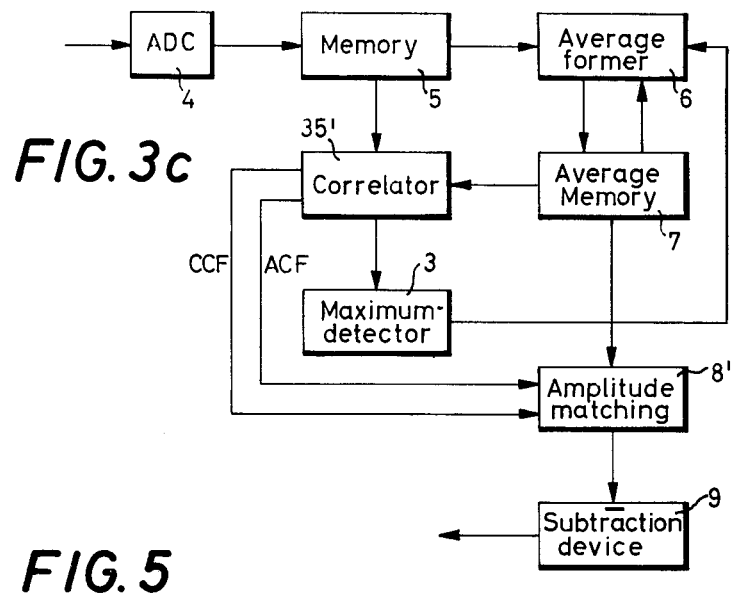
FIG. 3c is a block circuit diagram of a variation of the embodiment of FIG. 3a which can also be used together with the embodiment of FIG. 3b.

The block circuit diagrams shown in FIGS. 3a and 3c indicate how an apparatus for practicing the method of the invention can be constructed in principle. The person skilled in the art is familiar with the manner in which the individual stages, which are also shown in the subsequent drawing figures, can be realized by electronic circuits, since it is possible, for example, by means of instructions issued by component manufacturers, to arrive at a possible concrete embodiment for every circuit module named in FIG. 3. For example, this can be done according to the TTL, the CMOS or comparable techniques. Suitable embodiments of individual circuit groups are illustrated in detail in FIGS. 5 through 8 to which reference will be made in the detailed description of an embodiment.

FIG. 3b is a block circuit diagram of a further embodiment of an apparatus operating according to the present invention. In contradistinction to the embodiment shown in FIGS. 3a and 3c, the signals are here processed by microprocessors. For reasons of clarity two microprocessors are provided. Correspondingly, a single microprocessor can also be employed which then effects signal processing according to a time sharing method. The decision as to which one of the possibilities to choose depends on the further technical development, the number of units required, and on the requirements for operating speed, accuracy and reliability.

In the embodiment shown in FIG. 3a, the abdominally derived fetomaternal heart signal is fed to a preamplifier 1 which raises the low level of the input signal to a value that is sufficient for processing in subsequent stages.

A first improvement of the signal to noise ratio is effected by filtering in a bandpass filter 2. In the region of low frequencies the power of the maternal QRS complexes exceeds that of the fetal complexes to a considerable degree. The frequency components of the expected action potential of the maternal heart signal also lie in this range.

Between 15 and 40 Hz both signal powers are in approximately the same order of magnitude. Bandpass filtering with a pass band in this frequency range thus permits selective amplification of the fetal heart signal.

The lower and upper frequency limits of filter 2 are selected so that those frequency components of the received signal which do not contribute to the detection of the useful signal are suppressed. In the analysis of the fetal electrocardiogram there is a second criterion for determining the limits of the frequency band, i.e. that the maternal heart signal is attenuated but has a greater amplitude than the fetal signal so that it is possible to detect the maternal QRS complex by means of threshold value detectors.

Based on these considerations the frequency limits for the bandpass filter 2 in an advantageous embodiment of the invention are composed of a lower limit frequency of 15 Hz and an upper limit frequency of 40 Hz. Good results have been realized with the use of a nonrecursive digital filter of linear phase. Through a feedback connection from the output of the bandpass filter 2 to a control input of preamplifier 1 it is possible to effect an amplitude regulation of the preamplifier 1, to keep the triggering threshold for recognizing the maternal EKG at a constant value so that no further external amplitude setting is required.

In a preferred embodiment, a rectifier (not shown) is provided in the signal input so as to effect full wave rectification of the input signal without integration in a conventional circuit arrangement. This solution is of advantage during recording of myographic signals, i.e. signals derived from muscle movements which are a function of cardiac movements, if the input signal to be detected has no fixed polarity. This results in the advantage, for use in recording the fetomaternal electrocardiogram, that the electrodes need not be placed in every case so that only positive or only negative peaks can be expected and there is simultaneously made available a suitable control voltage for preamplifier 1. The further processing of the signals remains unaffected.

Figure 4:
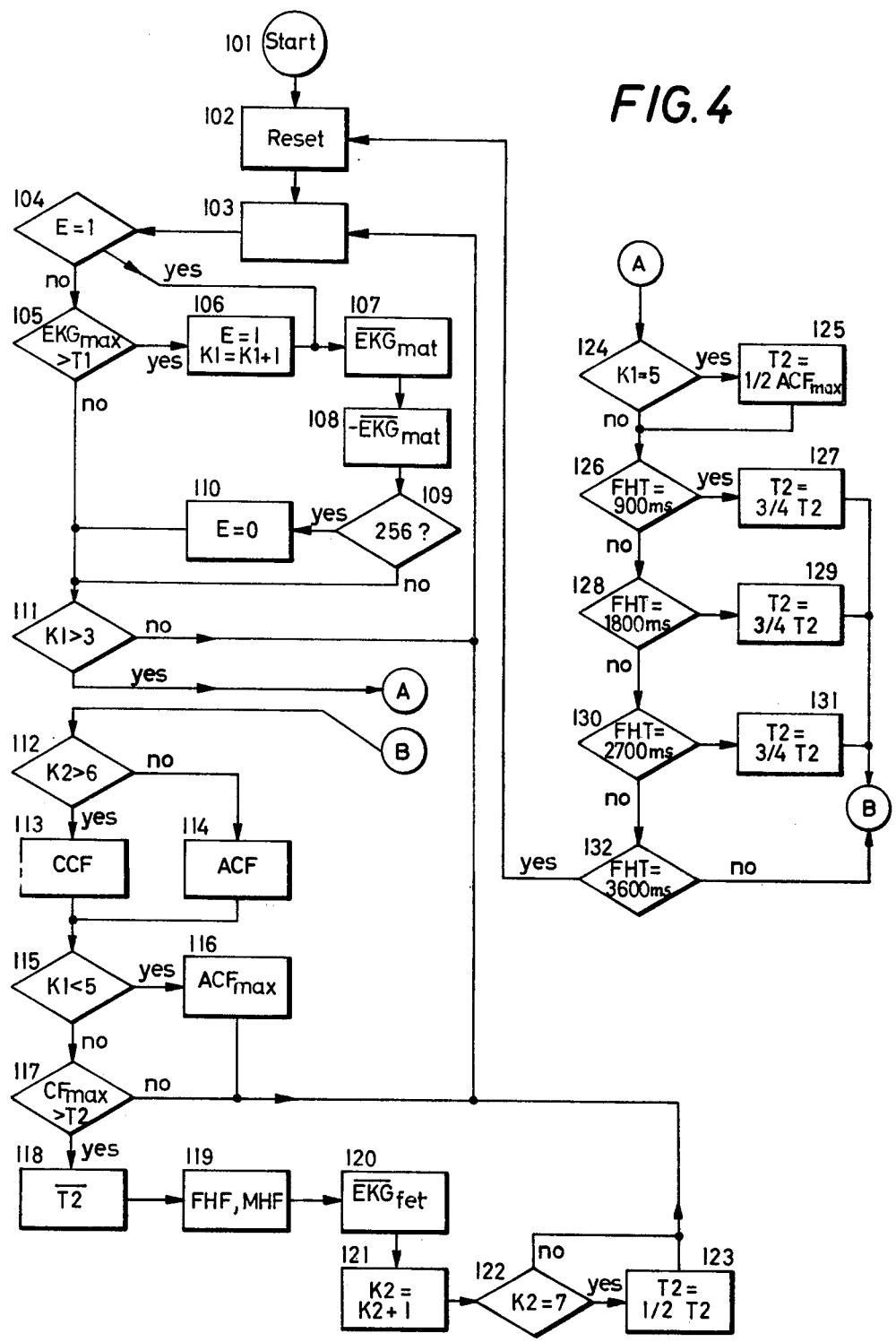
FIG. 4 is a flow diagram of the basic sequence of the method according to the present invention, providing a basis for a computer program which may serve, for example, to control a microprocessor.

FIG. 4 is a flow diagram of the course of the further signal processing in the individual blocks of the systems of FIGS. 3a and 3b. This flow diagram may constitute the basis for the development of the circuitry for a device employing discrete or integrated components and is only an example which can be modified according to individual requirements. The operational sequence can be permanently wired in, can be stored in ROM's or in programmed logic circuits and controlled accordingly. In order to explain the sequence of the further process of the invention, the following description refers to FIGS. 3a, 3b, 3c and 4 together and, insofar as details are concerned, also to FIGS. 5 through 9.

In order to realize sufficient reliability of detection of the QRS complexes during the analysis of the electrocardiograms, in the further steps of the detection process, the maternal heart signal, which in this case constitutes an interference signal, is subtracted from the entire abdominal signal before the cross correlation analysis is made. A prerequisite for this is that the maternal QRS complexes can be detected with certainty. For this purpose, the bandwidth of the preliminary filter is set so that the low frequency interference components and the high frequency interference components of the signals are sufficiently suppressed, the maternal electrocardiogram remains easily detectable and the fetal heart signal has its amplitude raised in addition.

By means of direct subtraction of an identified interfering signal component which is stored in the form of a sample signal that has been extracted from the preceding signal mixture, it is possible to effect an almost optimum interference removal.

The sample QRS complex required for the subtraction is determined by a weighted average formation in which the calculation of the maternal QRS sample and the subtraction are actuated by a trigger signal which indicates the occurrence of a QRS complex and is generated by a threshold value detector. This threshold value detector is provided in FIG. 3a in the form of a maximum or peak detector 3 or 3'. The maternal QRS complex is detected by the peak detector in a digital manner by unit 3 or in an analog manner by unit 3'. Due to the smaller amount of circuitry required, the analog solution is more advantageous, and is shown in FIG. 3a in dashed lines as an alternative.

Depending on the selected circuit embodiment, the signal for the maximum detector 3 or 3' is obtained downstream or upstream, respectively, of a conventional analog-digital converter 4. The analog-digital converter 4 operates in a known manner at a sampling frequency of 1 kHz. The filtered and digitalized fetomaternal heart signal provided by converter 4 is stored in a memory 5 and is fed from there to an average former 6. On occurrence of a trigger signal from the maximum detector 3 or 3', respectively, the average former 6 forms a new average, as soon as a new maternal QRS complex has been detected, from this new complex and from the sample of the maternal QRS complex already stored in an average memory 7, and the new average is subsequently fed into memory 7, where it is stored. In the starting state, the stored value may equal zero or any desired sample signal may be initially stored.

Figure 5:
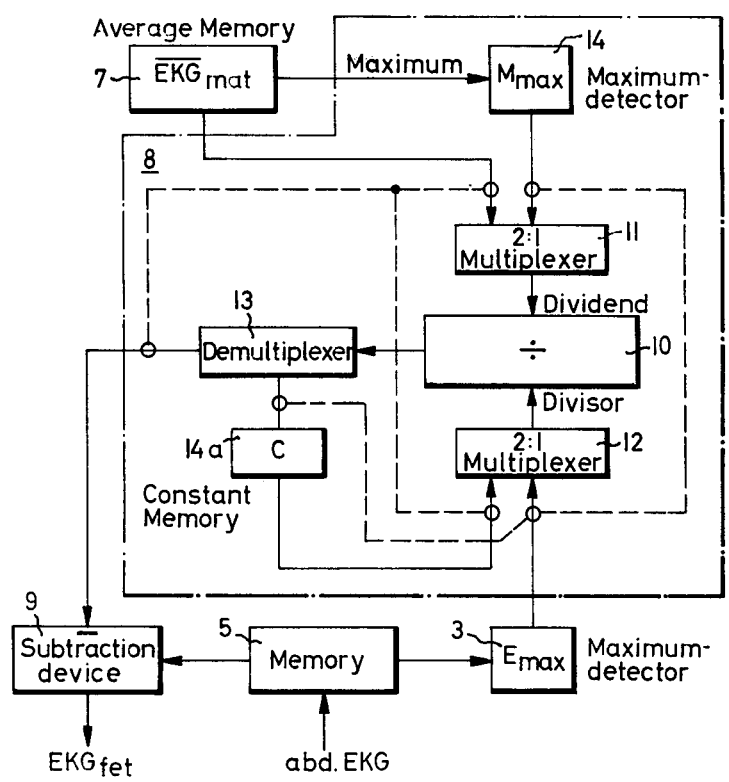
FIG. 5 is a block circuit diagram of a subtractor for use in apparatus for practicing the method according to the invention.

The maternal sample signal stored in memory 7 is processed in an amplitude matching device 8', one embodiment of which is shown in FIG. 5 together with the units with which it directly cooperates. The amplitude of the maternal sample signal stored in average memory 7 is adapted to the actual amplitude shape of the input signal by means of division by a scaling factor K in order to achieve as complete a separation as possible of the fetal heart signal from the maternal component.

The embodiment shown in FIG. 5 includes a conventional digitally operating divider 10 which receives the signals to be divided via multiplexers 11 and 12 in time alternation. The division result is provided via a demultiplexer 13. In addition, there is provided a maximum detector 14 for storing the amplitude of the actual maternal QRS complex and a memory 14a for storing the present value of the scaling factor K. The broken lines in FIG. 5 signify the simultaneous switching of the multiplexers 11 and 12 and the demultiplexer 13. The inputs and outputs connected by the dashed lines are activated at the same time.

The maximum value $\overline{EKG}_{mat}$ is transferred from memory 7 to detector 14 after each averging cycle, which in this configuration only functions as a memory for the value of the maximum detected. The relative (centered) position of the maximum within the sample remains unchanged in the memory 7.

When the maximum detector 3 signals the occurrence of a maximum of the maternal QRS-complex, this maximal value is loaded into the dividing device 10 via multiplexer 12. At the same time the maximum of the sample of the QRS-complex is loaded into the dividing device 10 via multiplexer 11. The resulting quotient is transferred into memory 14a. After that the configuration of the devices 11, 12 an 13 is switched into its second state. Subsequently each value of the points of the sample is divided by the constant registered in the memory 14a and subtracted from the value of the corresponding point of the abdominal EKG that is to be read from memory 5. After the values of all the points have been substracted, the amplitude matching device remains inoperative until the next maternal QRS-complex is detected.

The values of the sample points of the abdominal EKG are loaded successively into memory 5. After a maximum has been detected by detector 3, the address of the last entry into memory 5 is used for computing the address of the point that corresponds to the first point in memory 7. The sample is represented by the values of 256 points. The value of the maximum is numbered 128. By means of this convention synchronisation during subtraction is simplified by starting the subtractions wiith the value of point one of memory 7 and point "n minus 127" of memory 5, if the maximum has been detected for the value of the n-th point. The two last points are numbered 256 in memory 7 and "n+128" in memory 5. It has to be mentioned that the values of the points "n+1" until "n+128" are not immediately loaded into memory 5 after a maximum has been detected. They are transferred in a sampling mode in synchronism with the subtraction of the values of the first 128 points.

Figure 7A:
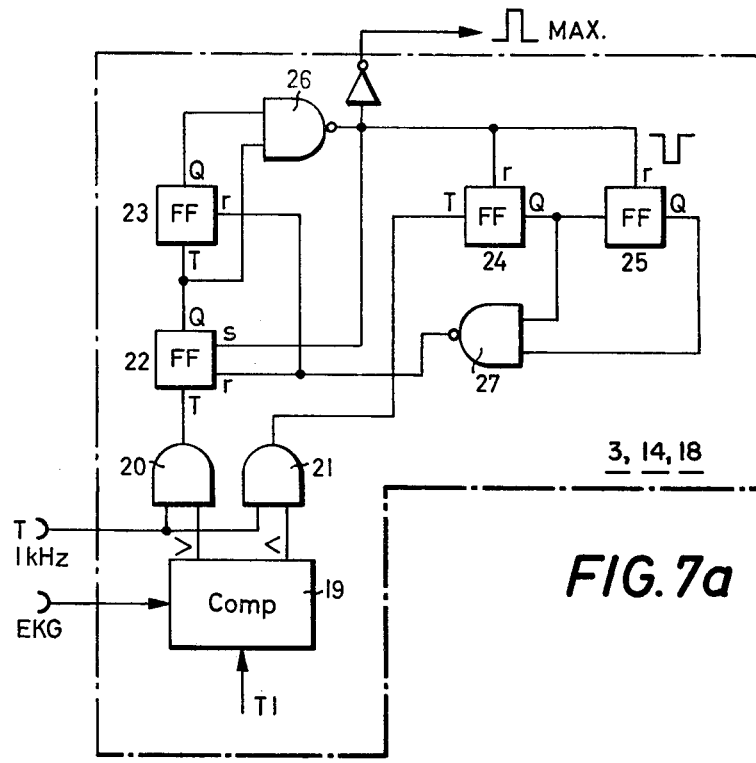
FIG. 7a is a circuit diagram of a maximum detector in digital design suitable for use in apparatus for practicing the method of the present invention.

The signals supplied to multiplexers 11 and 12 from detectors 14 and 3 are maximum values. The single value pulses shown in FIG. 7a are representations of these values, which are used as trigger pulses to control the transfer of the data to the processor (not shown) connected to the circuit displayed.

The amplitude matching device 8 together with the digital dividing device 10 included therein can be constructed from commercially available semiconductor devices, such as, for example integrated TTL circuits, according to the instructions provided by the semiconductor manufacturers.

The division result is supplied from demultiplexer 13 to subtraction device 9 together with the current abdominal EKG signal in memory 5 and there appears at the output of the subtraction device 9 the difference D representing the signal $EKG_{fet}$, which is formed as follows:

$$D = E - M/K$$

where
 $E$ = the actual abdominal EKG,
 $M$ = the sample of the maternal EKG; and
 $K$ = the scaling factor for amplitude matching during subtraction, the value for K being recalculated for each detected QRS complex from $$K = M_{max}/E_{max}$$

where $E_{max}$ is the amplitude of the actual maternal QRS complex; and $M_{max}$ is the amplitude of the maternal average value.

Figure 6:
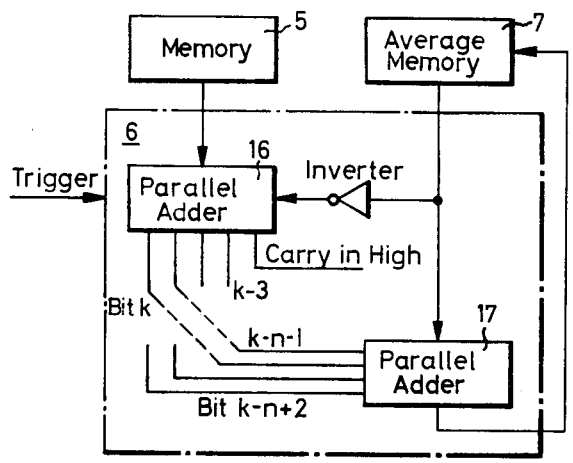
FIG. 6 is a block circuit diagram of an average former for use in apparatus for practicing the invention.

The average formation required for matching the stored signals to the actual signal shape at various points in the process, so as to "refresh" the contents of the memories in question, is shown in FIG. 6 according to its functional sequence. The illustrated blocks show the principle of how such a circuit can be realized. The average former 6 is shown in FIG. 6 together with those blocks of the system of FIG. 3a that surround it. The interior circuitry of block 6 shown there may just as well be used for the average former 15 of FIG. 3a, which will be described in detail below.

The average formation of the QRS complexes from the fetal or the maternal EKG is effected by exponential averaging according to the formulas:

$$M_n = \frac{E_n}{U} + \frac{U-1}{U} M_{n-1} \tag{4}$$

$$M_n = M_{n-1} + \frac{1}{U}(E_n - M_{n-1}) \tag{5}$$

where
 $M_n$ = the average value at time $t_n$;
 $M_{n-1}$ = the average value at time $t_{n-1}$;
 $E_n$ = the EKG at time $t_n$; and
 $U$ = an averaging constant.

In device 6, all values relate to the maternal EKG, in device 15 they relate to the fetal EKG.

The averaging constant determines the speed of matching of the stored values to the present signal shape. The value U should here be selected so that an optimum compromise is made between the improvement of the signal to noise ratio and the time constant for matching the EKG's to the actual wave shape. For digital implementation of the signal determination a power of two is selected for U because this makes the algorithm particularly easy to set up.

FIG. 6 is a schematic representation of an electronic circuit for calculating the signal average according to equation (5). In an parallel adder 16 the difference between $E_n$ and $M_{n-1}$ is formed according to the 2's complement method, the signal from memory 7 being supplied via an inverter. In a further parallel adder 17 the sum of the two components of the right-hand side of equation (5) is formed. Since U has the value of a power of two ($U=2^n$), the division of the difference component by U can be effected by shifting the bits of the difference produced by adder 16 to the right by n bit positions. If U is fixed, the division is permanently wired in by appropriately connecting the individual bits between the two adders as shown in FIG. 6. Upon appearance of a trigger signal from maximum detector 3 or 3', respectively, indicated by an arrow, a new average is formed each time. The selected embodiment affords high processing speeds at low cost. The illustrated method of exponential averaging results in an improvement of the signal to noise ratio by the factor $\sqrt{2U-1}$.

For a practical embodiment according to the TTL technique, integrated circuits of Type 7483 can be used as the parallel adders 16 and 17, Type 7404 for the inverter and Types 74,100, 74,199 etc. for the (EKG) memory 5 and the average value memory 7, depending on the length of the signal words.

The operation of a maximum detector that can be used for the process according to the invention and is present at various points in the disclosed circuits will now be described. In FIG. 3a, there are the maximum detectors 3, and 3' and 18, in FIG. 3b the maximum detector 3', and in FIG. 5, there is a maximum detector 14. In principle, it is possible to realize this system in digital or analog form. An embodiment of the digital form, as represented, for example, by the maximum detector 3 in FIG. 3a, is shown in FIG. 7a. In this detector the signal identified as "MAX" appears at the output when three voltage values of the input signal EKG measured at different times have exceeded the value of a triggering threshold T1, the measurement times being determined by an externally applied sampling pulse train "T" having a repetition rate of 1 kHz. The detector includes a counting unit which is reset to zero if another three measured values fall below the triggering threshold T1. Threshold T1 constitutes a variable parameter that can be adapted to the amplitude of the input signal of the circuit. The respective EKG signal is fed in digitalized form to the "EKG" input of a digital comparator 19 and is compared with the value of triggering threshold T1. If the EKG signal exceeds this triggering threshold, a signal appears at output ">", while if the signal stays below the triggering threshold a signal "<" is emitted. These signals are fed to respective AND gates 20 and 21. The output of each gate has a logic L if in addition to a 1 kHz clock pulse, a signal is also present at its associated comparator output.

Flip-flop circuits 22 and 23 as well as 24 and 25 together with NAND gate 26 and NAND gate 27, respectively, form two respective counters that each count to three and each counter is reset when the other counter emits a pulse upon reaching "three". Only the signal of the counter composed of D-flip-flops 22 and 23 which registers the exceeding of the threshold T1 is fed to the circuit output.

The output of maximum detector 3 in the configuration according to the embodiment shown in FIG. 7a signals the surpassing of trigger level T1 by the peak of the maternal QRS-complex. As the width of the positive pulse covers a certain time interval around the exact time position of the maximum, the matter is found by means of differentiating the analog input signal, where minimal differences between neighbouring values indicate the location of the maximum. The differentiation is carried out by the processor in the usual way.

Figure 7B:
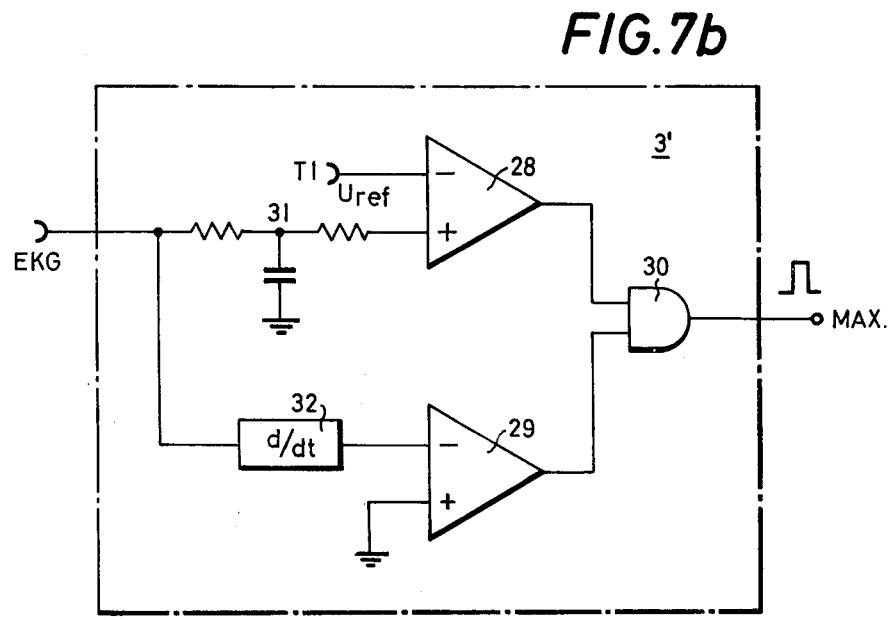

FIG. 7b shows a maximum detector for analog operation, which includes two operational amplifiers 28 and 29 as well as an AND gate 30. The input signal "EKG" is fed to the positive input of operational amplifier 28 via a lowpass filter 31 and to the inverting input of amplifier 29 via a differentiating member 32. The triggering threshold value T1 is applied to the negative input of the operational amplifier 28 as a reference level while the noninverting input of operational amplifier 29 is at ground potential. The logic "L" level appears at the output of the AND gate 30 when the signal "EKG" exceeds the amplitude value of T1 for a sufficiently long period of time and has a slope of zero value. As a whole, there appears the same effect as with the digitally operating maximum detector: T1 must have been exceeded at several points in time during the duration of the input signal "EKG," it being a prerequisite that the latter has taken on an extreme value.

In the circuit for practicing the method as shown in FIG. 3b several of the evaluation functions described above are preferred by a microprocessor 33. The modules corresponding to blocks 1 through 4 are identical with those of the circuit shown in FIG. 3a. The peripheral components of the microprocessor 33 include the average memory 7 and the amplitude matching device 8 which also take over the same functions as in the circuit according to FIGS. 3a and 3c, respectively, but with respect to the processing of data are adapted to the special microprocessor employed in the circuit. At the output of microprocessor 33 there appears the fetal heart signal which has been separated from the maternal component.

The microprocessor 33 is programmed according to the flow diagram shown in FIG. 4 which represents a generally preferred embodiment of a program for the process according to the invention and which can also be used for practicing the process in the same or a similar manner in devices designed according to other techniques, such as discrete, TTL, CMOS, etc.

The program for operation of the system starts, as shown in FIG. 4, at "Start" 101. This resets all counters and memories in block 102, which simultaneously is the point of entry for a program loop, then proceeds to block 103 in which a voltage value of the abdominally derived EKG is written in during a cycle time of 1 ms, corresponding to a scanning or sampling or clock pulse rate of 1 kHz. A branch instruction 104 then causes the value of a flag E to be checked. If E equals zero, which is equivalent to the fact that no maternal QRS complex has been recognized and is being processed, it is determined in a further branch 105 whether the input "EKG" exceeds the triggering threshold T1, this corresponding to the function of the previously described maximum detector. If T1 has not been exceeded, it is determined in a branch 111, whether the value K1, corresponding to the number of detected maternal complexes, is greater than three. If this is not the case, the program sequence jumps back to block 103.

If the value of $EKG_{max}$ has exceeded the triggering threshold T1, a program block 106 is entered from branch 105. Since exceeding of the triggering threshold T1 is synonymous with the recognition of a maternal QRS complex, the flag E is set to one and the value K1, the number of detected maternal complexes, is raised by one, i.e. from zero to one. If E equals one, the subsequent EKG values need no longer exceed the triggering threshold T1, and the program sequence proceeds directly from block 104 to the now following block 107 in that the averaging of the maternal EKG is effected as described above in connection with the average former. The averaging is effected individually for each scanned EKG value.

In the next block 108, the averaged $EKG_{max}$ value is subtracted from the currently measured value, the subtraction being made with amplitude matching as described in connection with FIG. 5. In the subsequent branch 109 a check is made as to whether the described averaging and subtraction has already been effected for the entire expected duration of a maternal QRS complex. For this purpose the number of measured values that have been read in since the flag E was changed from zero to one is counted. If 256 values have been measured, the detection of a maternal QRS complex is considered to be completed and the program proceeds from branch 109 to block 110 at which the flag E is reset to zero so that for the renewed activation of the subtraction process it will again be necessary that the input signal exceeds the triggering threshold T1.

The number of averages of the maternal complex $EKG_{mat}$ which must be exceeded so that a reliable average of the maternal complex is available for separating the abdominally derived heart signal from the maternal component, will advisably be selected to be higher than three. In the program sequence shown in FIG. 4 K1 has been assumed to be three for reasons of clarity. The averaging constant U for the exponential averaging of $EKG_{mat}$ is advisably higher than or equal to eight. If, due to the favorable calculation afforded for digital signal processing, a power of 2 is selected, U=16 is a preferred value. During subtraction (block 108) the sample signal that has been formed by averaging in the preceding cycle is used as a basis so that the actual section of the signal curve does not influence the suppression of the maternal heart signal. Otherwise there would exist the danger that the desired fetal heart signal would also be suppressed. Matching the amplitude of the average value with the amplitude of the input signal significantly contributes to an improvement of the signal evaluation since, particularly at the onset of the averaging procedure, the sample and the momentarily present QRS complex may differ significantly in amplitude. Due to the fact that only one measured value is subtracted and averaged from the signal section per cycle, the process can be realized with particularly economical equipment since the required computing speed has been reduced.

The basic sequence of the further processing of the signals will now be explained with the reference to FIG. 3a. The abdominally recorded heart signal portion, containing predominantly the fetal EKG, which has been separated from the maternal QRS complex is now fed to a memory 34 from which the further processing branches out. On the one hand, the signal is fed to a correlator 35 which is able to perform an autocorrelation as well as a cross correlation calculation in dependence on the type of process involved, as will be explained in detail below. The average former 15 produces a sample of the fetal EKG in a manner similar to that in which the average former 6 produced a sample of the maternal QRS complex. The resulting calculated average of the fetal EKG is retained in an average memory 36. The values contained therein are used by the correlator 35 to form the cross correlation function with the input signal.

The maximum detector 18, which is connected to the output of correlator 35, senses the maxima of the correlation function which is equivalent to the occurrence of a fetal QRS complex and thus triggers the formation of a revised average of the fetal electrocardiogram in the average former 15. The formation of the average itself is here again effected exponentially.

In the starting phase, when the average of the fetal EKG cannot as yet be utilized, correlator 35 forms an autocorrelation function and when there is a maximum in this function, the average former 15 is put into operation. Upon completion of this starting phase, when the calculated average $\overline{EKG}_{fet}$ approximates the actual fetal EKG with sufficient accuracy to be used as a sample, the correlator 35 forms the cross correlation function of the current EKG with the averaged sample that has been obtained by exponential determination as the reference signal. From the time interval between the maxima of the autocorrelation function and of the cross correlation function the fetal heart frequency is determined in function block 37.

If the demands for reliability of the process are reduced, the detection of the fetal QRS complex can also be effected without correlation. In this case the preprocessed signal is fed directly to the maximum detector 18, i.e. there exists a direct connection between blocks 34 and 18 with elimination of blocks 15, 35 and 36.

Figure 8:
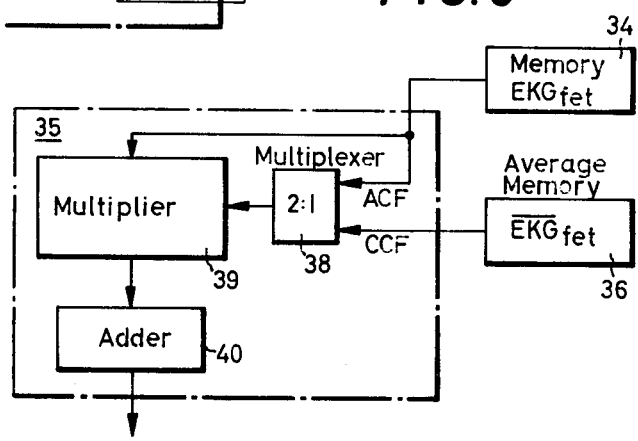
FIG. 8 is a block circuit diagram of a correlator suitable for use in apparatus for practicing the method of the present invention.

FIG. 8 shows a block circuit diagram of an embodiment of the correlator 35 for use in the process of the present invention. The signal $EKG_{fet}$ which has been separated from the maternal component simultaneously enters a multiplexer 38 and a rapid multiplier 39, that has been designed according to the TTL technique, in order to form the autocorrelation function. In order to likewise be able to perform a cross correlation, the other input of the multiplexer 38 receives the average of the fetal heart signal $\overline{EKG}_{fet}$ from average memory 36. The autocorrelation and cross correlation products are thus formed alternatingly. The respective correlation integral itself is calculated by an adder 40 downstream of multiplier 39 and is fed to maximum detector 18 of FIG. 3a.

Figure 9:
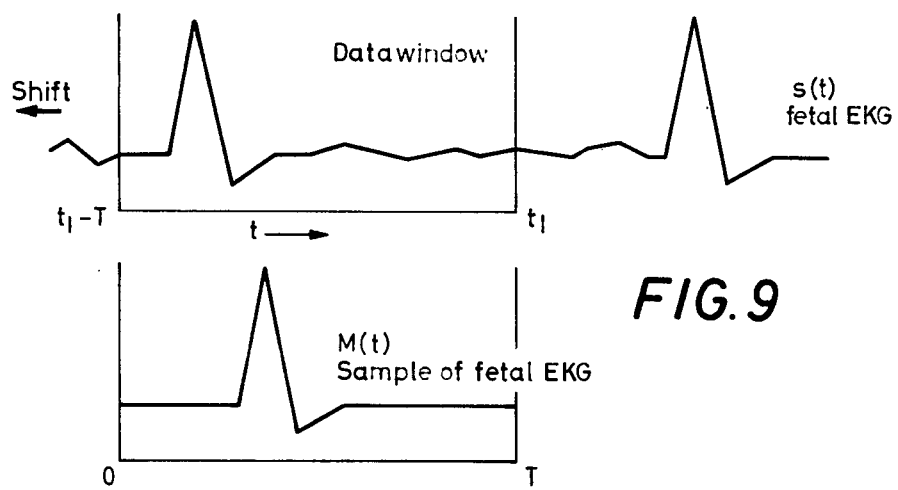
FIG. 9 is a schematic waveform representation of the formation of a cross correlation function.

FIG. 9 is a schematic representation of the formation of the cross correlation function between a stored sample signal and the currently recorded heart signal for the example of the fetal EKG. The time period covered by the integration is identified as the "data window" and in successive observations the signal curve s(t) moves in the direction of the arrow with respect to the data window. The correlation functions may be formed according to known methods such as those employed, for example, in the Model 3721A correlator made by Hewlett Packard.

In the apparatus for practicing the method employing microprocessors as shown in FIG. 3b, the signals are processed correspondingly. A microprocessor 41 receives input signals from block 34 and is in communication with the average former 15, the average memory 36 for $\overline{EKG}_{fet}$ and the correlator 35. These units are of course also adapted to the microprocessor employed. The latter, for example, may perform the calculations required for the various stages in a time sharing process and obtain the required signal values. From the available data it computes the fetal heart frequency according to a given program.

Program blocks 112 to 123 of FIG. 4 show the course of a correlation analysis which is suitable for operation of a microprocessor or generally of an electronic data processing system. A conclusion as to the presence of a fetal QRS complex is made if the value of the correlation function produced by correlator 35 exceeds a triggering threshold T2, determined by detector 18. It is advisable for this triggering threshold T2 to adapt itself to the changing signal amplitudes since only in this way will dependable detection be assured. Since the shape and amplitude of the fetal electrocardiogram is not known beforehand, an amplitude value cannot be set beforehand for the triggering threshold T2. Before evaluatable measurements can be made, a certain period of time is used to search in the signal mixture that has been separated from the maternal complex to locate the fetal complex, and its maximum is determined. The period of time between three successive maternal QRS complexes is used for this purpose.

If the program sequence between points A and B in the flow diagram of FIG. 4 is left unconsidered for the moment, the program moves from branch 111 to a branch 112 if the number (K1) of determined maternal complexes is greater than three. In branch 112 it is determined whether the number (K2) of detected fetal complexes is greater than six. On the assumption that the program sequence is still in the starting phase so that no fetal heart signal has been detected as yet, the autocorrelation function of the signal mixture separated from the maternal component is calculated in block 114. The maxima of this autocorrelation function are determined according to branch 115 and block 116, the program then returning to block 103, until the fifth maternal complex (K1=5) has been found. The autocorrelation function is calculated only for a delay of $\tau=0$ from a signal interval of 200 ms.

The program portion taking place between points A and B serves, inter alia, to fix and influence the triggering threshold T2. When the fifth maternal complex has been determined, i.e. K1 equals five, the program continues over a branch 124, where this value of K1 is sensed, and block 125 where the amplitude value of triggering threshold T2 is set to half the value of the greatest maximum of the autocorrelation function occurring in correlator 35 during the time between the third and fifth maternal complexes.

In the now following signal processing the autocorrelation function is still calculated via branch 112 and block 114, but since the number of maternal complexes has now reached five, a branch 117 determines whether the maximum of the formed correlation function ($CF_{max}$) exceeds the value of the triggering threshold T2—which had been set to half the value of the previously formed autocorrelation function. If this is not the case, the program jumps back to block 103. If it did exceed it, the triggering threshold is brought up to the amplitude shape of the signal by means of exponential averaging. T2 is thus set so that it always takes on half the valiue of the average correlation maximum. This likewise optimally adapts the sensitivity of the system to the actually prevailing signal conditions. From the correlation function, the fetal heart frequency (FHF) and the maternal heart frequency (MHF) as well are calculated in block 119.

According to block 120, the fetal heart signal is averaged exponentially and stored in an average memory. This sample serves for the later calculation of the cross correlation function with the actual signal in block 113. Thus a fetal heart signal has been determined and the value of K2 which indicates the number of detected fetal complexes, is upped by one according to block 121.

After a further starting phase the sample of the fetal heart signal as calculated by average formation is accurate enough to serve as a reference signal for the calculation of the cross correlation function of the fetal electrocardiogram. The occurrence of seven fetal QRS complexes is considered to be sufficient. If K2 is greater than six, branch 112 directs the program to block 113 and the cross correlation function is now determined in the described manner.

Since, if the averaging constant is selected to be U=16, the amplitude of the computed sample of the fetal heart signal has not as yet reached its final value after seven passages, the maxima of the cross correlation initially have a lower value than those of the previously calculated autocorrelation function. Therefore the triggering threshold T2 is set to half its previous value when a change is made from calculating the autocorrelation function to calculating the cross correlation function. This is accomplished in that the program sequence for K2=7 is directed from branch 122 to a block 123 where the above-mentioned reduction of the triggering threshold T2 is effected.

If the amplitude of the fetal heart signal decreases so rapidly during the analysis that the average formation cannot follow the triggering threshold T2 in block 118, or if the fetal heart signal changes in shape, the amplitude of the correlation function will no longer exceed the triggering threshold T2. In that case the value of T2 is reset to 0.75 of its original value if no fetal QRS complex was detected for 900, 1,800 and 2,700 ms. If the triggering threshold was not exceeded for 3.6 seconds, all parameters and samples are erased and the algorithm is started anew. The program sequence required for this is contained in function blocks 126 to 132 between points A and B in FIG. 2. Resetting of the triggering threshold T2 to 0.75 of its original or previous value is effected in blocks 127, 129, and 131 after the respective periods have expired without the triggering threshold having been exceeded and this in dependence on the results in branches 126, 128, 130 which are associated with the respective time periods as shown in FIG. 4.

The operations carried out by the elements 119 and 124 to 132 are performed by means of circuits that are set up according to examples given in the applications published by leading semiconductor manufactures. For an embodiment that is making use of TTL-integrated circuits, examples may be chosen from the publication "Designing with TTL Integrated Circuits." According to the functions of the individual elements that may be seen from the description of the flow chart counters (7493 e.g.), comparators (7485 e.g.), shift registers and one or more arithmetic logic units (SN 74181) may be used.

FIG. 3c shows a variation of the two described embodiments of the method according to the invention, which variation differs from the previously described embodiments in the manner of determining the average of the maternal EKG and in the determination of the scaling factor K during subtraction of the stored average from the actual signal shape.

The stages shown in FIG. 3c replace the stages 3 to 9 of FIG. 3a. The basic function of the illustrated modules corresponds to that of modules 15, 18 and 34 to 36 of FIG. 3a with the difference that it is not the fetal electrocardiogram that is determined and stored for the purpose of calculating the fetal heart frequency, but rather the maternal electrocardiogram which is subtracted from the input signal for the purpose of separating it from interference. No differences exist in the basic signal processing with respect to initial detection of the heart signal and the continuous correction or adaptation by way of average formation. Each stage whose function coincides with that of a corresponding stage of previously described embodiments is identified with the same reference numeral.

The input signal again passes through an analog-digital converter 4 into memory 5 in which the pattern or waveform of a segment of the actual input signal is stored. A correlator 35' is provided which corresponds to that shown in FIG. 8, with the exception that the input signals to correlator 35' are derived from stages 5 and 7 instead of stages 34 and 36. Correspondingly, in a starting phase of the measurement, the maximum of the autocorrelation function is determined and the associated heart signal is stored in average memory 7. Thereafter the averaged signal, triggered by occurrence of the maximum of the cross correlation function, is adjusted by a newly detected maternal heart signal by way of averaging, the function of average memory 7 corresponding to that of stage 7 of FIG. 3a.

A further difference from the embodiment shown in FIG. 3a is that in this variation of the method according to the invention, there is provided on amplitude matching device 8' which serves to adapt the amplitude of the average maternal electrocardiogram, which is to be subtracted, to the actual amplitude of the then occurring input signal so that this signal component is removed from the signal mixture. The circuit employed differs from the amplitude matching device 8 shown in FIG. 5 only in that instead of the values $M_{max}$ (stage 14) and $E_{max}$ (stage 39 the autocorrelation function and the cross correlation function are processed, the quotient K of the two values being formed alternatingly and, on the other hand, the average value of the maternal heart signal stored in stage 7 is divided by this value K. The subtraction device 9 thus precisely corresponds in its operation to that shown in FIG. 3a. The mathematical derivation to obtain the scaling factor K for this variation has been explained above. The advantage is here that the available correlator 35' can be utilized for two different functions, its time control in the sense of a multiplex operation being known.

An additional simplification results if the variation of the process illustrated in FIG. 3c is transferred to the embodiment shown in FIG. 3b. In this case the function of the microprocessor 33 must merely be supplemented by the function of the correlator 35' of FIG. 3c. Stage 3' is eliminated because the maximum detection with respect to the CCF, or in the starting phase with respect to the ACF, respectively, is taken over by the microprocessor circuit itself. Since the detection process for the maternal heart signal corresponds to that for the fetal heart signal, the program for the microprocessor circuit can refer back to the signal shape shown in FIG. 4 between stages 112 and 120. The function of correlators 35' and 35 can here advantageously be taken over by a single function group which operates in multiplex.

A few particularities must be observed during the detection of the fetal QRS complexes by determination of the maxima of the correlation function. Calculation of the CF significantly improves the signal to noise ratio of the signal but it is impossible to completely suppress the noise components. Since, due to fluctuations in the amplitude of the fetal heart signal and thus of the correlation function, the triggering threshold T2 must be kept relatively low, it is possible that ancillary maxima under the influence of interference already exceed the threshold and lead to erroneous triggering.

In order to avoid this it is of advantage of search, within a time period of 100 ms after occurrence of a maximum, for a further higher maximum. For this purpose the triggering threshold T2 is set, once a maximum has been detected, to the value of this maximum until one or more further maxima have been found. At the end of a time of 100 ms after detection of the highest maximum, T2 is set back to its normal value. The time-dependent regulations are not shown in the block circuit diagrams of FIGS. 3a to 3c and 5 to 8. However, the necessary switching means can be realized by way of known logic circuits.

Prerequisite for the average formation of the fetal and maternal EKG is that the formed and stored sample function and the actual signal shape are not offset in time during point-by-point scanning. For that reason, the sample and actual signal are continuously scanned as to their maximum or peak value during average formation for the maternal heart signal. Averaging is effected only if both signals are in the same phase, i.e. the maxima coincide in time. The correlation analysis triggers the average formation of the fetal heart signal when there is a maximum. While phase equality is assured during calculation of the cross correlation function, a phase shift may occur during calculation of the autocorrelation function. In order to avoid faulty triggering in this case, sample and signal are additionally scanned for their maximum values during analysis by means of autocorrelation. The two maxima are then synchronized in order to form the average.

The preceding is a description of the process according to the invention and of apparatus for practicing the process, using as an example the detection of fetal heart signals in an abdominally derived signal mixture of maternal and fetal heart signals in which the maternal signals far exceed the fetal signals in amplitude. The described process also has significant advantages in the detection of many other kinds of masked signals in which similar problems exist, such as, for example, myographically derived signals. Adaptation and selection of individual advantageous embodiments of the method suitable for the particular problem at hand which, in particular, can be adapted to the particular type of fluctuation in fluctuating signal amplitudes, are within the competence of the person skilled in the art. The particular fields of application and advantages can be derived from the above description of the example of the detection of fetal heart signals since the respective problems and the solutions found therefor can be generalized without difficulty.

The two appended programs "KORA 1 and 2" have been used with the method described in connection with two cooperating microprocessors of the Type CP 1600 (manufactured by GI and ITT repectively). The program has been printed with the source program in assembler form, while the object program is listed on the left, according to the General Instrument developing system "GIMINI". The respective manuals and publications may be referred to for further details. Remarks and explanations referring to different parts of the program are in German language.

The inputs and outputs addressed by the program belong to the peripherals connected to the microprocessors. These addresses also serve for the transfer of data between the two processors and are listed seperately in the top of the programs.

The peripheral units are digital-analog and analog-digital converters serving for the transmission and the reception of data in connection with the method for detecting signals described. The communication between the two processors is carried out by means of transfer registers.

A version of the time dependent threshold variation described in connection with the flow chart of FIG. 4 in microprocessor program form is listed in program "KORA 2" under #129-address 204 of the object program-(setting the trigger level on the maximal value) and #206 to 212 - addresses 365 to 375 of the object program-(adaptive following of the trigger level as performed by block 118 in FIG. 4).

It will be understood that the above description of the present invention is susceptible to various modifications, changes and adaptations, and the same are intended to be comprehended within the meaning and range of equivalents of the appended claims.

What is claimed is:

1. A method for identifying a periodically recurring signal pattern contained in a signal mixture which also contains interference components, comprising: detecting the amplitude pattern of a segment of the signal mixture according to a first criterion; storing the detected pattern in a memory, where the stored pattern constitutes a sample; continuously matching the amplitude pattern of the stored sample to subsequently occurring signal mixture segments having a similar amplitude pattern; and determining the degree of coincidence between the amplitude pattern of subsequently occurring signal segments and that of the sample in order to identify such subsequently occurring segments according to a second criterion, which is different from the first criterion.

2. A method as defined in claim 1 wherein the signal pattern to be detected is a fetal heart QRS complex and the signal mixture is a fetomaternal electrocardiogram.

3. Method as defined in claim 1 wherein said step of matching comprises averaging the corresponding amplitude values of the stored sample and of a subsequently occurring segment, and said step of storing includes thereafter storing the averaged amplitude shape as the sample.

4. Method as defined in claim 3 wherein said step of averaging is effected for a given period of time from signals which have been detected exclusively according to the first criterion before said step of determining.

5. Method as defined in claim 1 further comprising removing interference components from the signal mixture before step of detecting.

6. Method as defined in claim 5 wherein said step of removing interference components is carried out by filtering out predetermined interference components.

7. Method as defined in claim 5 comprising, before said step of detecting, preliminarily detecting a first occurrence of a periodically recurring interference component signal according to a third criterion, preliminarily storing the amplitude pattern of such signal in a second memory, subsequently detecting the occurrence of a further identical interference signal in the signal mixture, and, as soon as the occurrence of such a further identical interference signal, subtracting this further signal from the amplitude pattern stored in the second memory in identical phase with respect to its amplitude.

8. Method as defined in claim 7 wherein said step of subsequently detecting is carried out according to a second criterion by determining the degree of coincidence of the signal mixture with the amplitude shape of the interference signal that is stored in the second memory.

9. Method as defined in claim 7 wherein the interference signal is subject to long term amplitude variations, and said step of preliminarily storing in a second memory includes continuously adjusting the amplitude pattern stored in the second memory to the current signal shape of the interference signal.

10. Method as defined in claim 7 wherein said step of preliminarily storing in a second memory comprises averaging the corresponding amplitude values of the stored interference signal and of the currently detected interference signal and storing the averaged amplitude shape, thereby creating an improved matching of the stored amplitude pattern of the interference signal with the pattern of later interference signals that have been detected.

11. Method as defined in claim 10 wherein said step of subtracting is effected only if averages of the amplitude pattern of the interference signal have been obtained for a predetermined period of time.

12. Method as defined in claim 7 wherein the third criterion is that at least one of the amplitude pattern and autocorrelation function of the signal mixture exceeds a selected threshold value, and comprising adjusting the magnitude of the selected threshold value to the average amplitude of the interference components contained in the signal mixture.

13. Method as defined in claim 12 wherein said step of adjusting comprises providing a scaling factor for the amplitude of the interference components, which is a function of the ratio of the cross correlation function of the pattern stored in the second memory and the signal mixture to the autocorrelation function of the pattern stored in the second memory.

14. Method as defined in claim 12 wherein said step of adjusting comprises providing a scaling factor for the amplitude of the interference components, which is a function of the ratio of the cross power of the pattern stored in the second memory and the signal mixture to the power of the pattern stored in the second memory.

15. Method as defined in claim 1 wherein said step of determining includes adapting the amplitude level of the sample to the amplitude level of the signal mixture.

16. Method as defined in claim 15 wherein said step of adapting is carried out with respect to the maximum values of the amplitudes of the sample and signal mixture.

17. Method as defined in claim 1 wherein the first criterion is that at least one of the amplitude pattern and the autocorrelation function of the signal mixture exceeds a given threshold value.

18. Method as defined in claim 1 comprising varying the given threshold value according to the average amplitude of the signal mixture.

19. Method as defined in claim 17 comprising varying the given threshold value in accordance with the amplitude of the signal sample stored in the memory.

20. Method as defined in claim 17 comprising varying the given threshold value according to the amplitude of the autocorrelation function.

21. Method as defined in claim 17 comprising reducing the given threshold value in amplitude whenever the existing threshold value has not been exceeded for a certain period of time.

22. Method as defined in claim 17 wherein the second criterion is that the cross correlation function formed between the signal mixture and the amplitude pattern of the stored sample exceeds a second given threshold value, and comprising revising the amplitude of the second threshold value when a change is made from evaluation of the autocorrelation function to evaluation of the cross correlation function.

23. Method as defined in claim 1 wherein the first criterion is that at least one of the amplitude pattern and autocorrelation function of the signal mixture reaches a maximum.

24. Method as defined in claim 1 wherein the second criterion is that the cross correlation function formed between the signal mixture and the amplitude pattern of the stored sample exceeds a given threshold value.

25. Method as defined in claim 24 comprising varying the given threshold value according to the average amplitude of the signal mixture.

26. Method as defined in claim 24 comprising varying the given threshold value according to the amplitude of the cross correlation function.

27. Method as defined in claim 24 comprising reducing the given threshold value in amplitude whenever the existing threshold value has not been exceeded for a certain period of time.

28. Method as defined in claim 1 wherein the second criterion is that the cross correlation function formed between the signal mixture and the amplitude pattern of the stored sample reaches a maximum.

29. A method as defined in claim 1 wherein the signal pattern is subject to long term amplitude variations and said step of continuously matching comprises exponentially averaging the corresponding amplitude values of the sample and of the current signal, and thereafter storing the averaged amplitude shape as the sample.

30. A method as defined in claim 29 wherein said step of exponential averaging comprises employing an averaging constant whose value is a whole number power of two.

31. A method as defined in claim 30 wherein the value of the averaging constant is sixteen.

32. A method as defined in claim 1 wherein said step of determining comprises effecting a signal evaluation for individual amplitude values of the signal pattern separately by a repeated calculation.

33. A method as defined in claim 1 wherein the signal pattern is subject to long term amplitude variations, and said step of storing includes continuously averaging the sample and the current signal only when their amplitude maxima occur in time coincidence.

34. A method as defined in claim 1 wherein the signal pattern to be detected is a fetal heart signal, the signal mixture is an abdominally derived fetomaternal electrocardiogram, and comprising measuring the fetal heart frequency from the time spacing between the maxima of the degree of coincidence occurring during said step of determining.

35. A method as defined in claim 1 wherein the signal pattern to be detected is a fetal heart QRS complex subject to long term amplitude variations, the signal mixture is a fetomaternal electrocardiogram, and said step of continuously matching comprises averaging the corresponding amplitude values of the sample and of the subsequently occurring signal mixture segments for a given period of time from signals which have been detected exclusively according to the first criterion before the second criterion is used for the detection of signals, and thereafter storing the averaged amplitude shape of the sample.

36. A method as defined in claim 35 wherein the given period of time corresponds to the occurrence of a predetermined number of maternal QRS complexes.

37. A method as defined in claim 35 wherein the given period of time corresponds to the occurrence of a predetermined number of fetal QRS complexes.

38. A method as defined in claim 1 wherein the signal mixture is constituted by myographically sensed signals.

39. A method as defined in claim 38 comprising the step of rectifying the signal mixture before said step of storing.

40. Method as defined in claim 1 wherein the first criterion is that at least one of the amplitude pattern and the autocorrelation function of the signal mixture remains above a selected threshold during a given time interval and passes through a maximum.

41. Method as defined in claim 1 wherein the second criterion is that the magnitude of the cross correlation function formed between the signal mixture and the amplitude pattern of the stored sample remains above a selected threshold during a given time interval and passes through a maximum.

42. A method for identifying a periodically recurring first signal pattern contained in a signal mixture which also contains a periodically recurring second signal pattern having a larger average amplitude than the first pattern, comprising: detecting the second signal pattern in the signal mixture according to a first criterion; storing the detected second pattern; subtracting the stored pattern from subsequent occurrences of the second pattern in the signal mixture to form a difference signal; detecting the first signal pattern in the difference signal according to a second criterion; and determining, according to a third criterion, the degree of coincidence between the amplitude pattern of subsequently occurring difference signal segments and the detected first signal pattern.

43. Apparatus for identifying a periodically recurring first signal pattern contained in a signal mixture which also contains a periodically recurring second signal pattern having a larger amplitude than the first pattern, comprising: first detecting means for detecting the second signal pattern in the signal mixture according to a first criterion; memory means connected to said first detecting means for storing the detected second pattern; arithmetic means connected to said memory means and to said first detecting means for subtracting the pattern stored in said memory means from subsequent occurrences of the second pattern detected by said first detecting means to form a difference signal; second detecting means connected to receive the difference signal and to detect the first signal pattern therein according to a second criterion; and signal processing means connected to said second detecting means for determining, according to a third criterion, the degree of coincidence between the amplitude pattern of subsequently occurring difference signal patterns and the detected first signal pattern.

* * * * *